(12) United States Patent
Carpenter et al.

(10) Patent No.: US 6,581,889 B2
(45) Date of Patent: Jun. 24, 2003

(54) FLEXIBLE STABILIZER ARM FOR FORCIBLY HOLDING AN OBJECT AGAINST A SURFACE

(75) Inventors: Kenneth W. Carpenter, La Jolla, CA (US); Michelle Fourmont, Carlsbad, CA (US); Kazuo Sasamine, Lemon Grove, CA (US)

(73) Assignee: Medivas, LLC, San Diego, CA (US)

( * ) Notice: Subject to any disclaimer, the term of this patent is extended or adjusted under 35 U.S.C. 154(b) by 67 days.

(21) Appl. No.: 09/758,585

(22) Filed: Jan. 10, 2001

(65) Prior Publication Data

US 2001/0025905 A1 Oct. 4, 2001

Related U.S. Application Data

(60) Provisional application No. 60/175,300, filed on Jan. 10, 2000.

(51) Int. Cl.[7] .............................................. F16M 13/00
(52) U.S. Cl. .................. 248/160; 248/231.71; 600/227; 600/37
(58) Field of Search ................................ 248/160, 104, 248/81, 274.1, 231.71; 600/233, 227, 229, 230, 37

(56) References Cited

U.S. PATENT DOCUMENTS

| | | | | |
|---|---|---|---|---|
| 3,858,578 A | * | 1/1975 | Milo | 128/20 |
| 5,899,425 A | | 5/1999 | Corey, Jr. et al. | 248/276.1 |
| 5,947,896 A | | 9/1999 | Sherts et al. | 600/229 |
| 5,980,569 A | * | 11/1999 | Scirica | 623/2 |
| 6,007,486 A | | 12/1999 | Hunt et al. | 600/205 |
| 6,036,641 A | | 3/2000 | Taylor et al. | 600/231 |
| 6,102,853 A | * | 8/2000 | Scirica et al. | 600/227 |
| 6,120,436 A | * | 9/2000 | Anderson et al. | 600/201 |
| 6,213,941 B1 | | 4/2001 | Benetti et al. | 600/235 |
| 6,264,605 B1 | * | 7/2001 | Scirica et al. | 600/227 |

* cited by examiner

*Primary Examiner*—Gwendolyn Baxter
(74) *Attorney, Agent, or Firm*—Gray Cary Ware & Freidenrich, LLP; June M. Learn (57) ABSTRACT

A flexible stabilizer arm assembly is provided that can be positioned in a desired three-dimensional attitude and then fixed in place to forceably hold an object against an undulating surface. In one embodiment, the invention assembly comprises a mounting base for attachment of the arm to a stationary fixture, a flexible arm of multiple articulated elongate links rotatably joined to adjacent links, a freely rotatable turret joint at the distal end of the arm that is adapted to attach an appendage in freely rotatable fashion to the distal end of the arm. Once positioned, a tightening mechanism is actuated to fix the attitude of the arm with respect to the mounting base. Optionally, the appendage is a two-tined foot adapted for holding a surgical instrument, such as a suction body, against a beating heart. The flexible arm, which ranges up to 12 inches in length, can withstand an undulating force exerted against the distal end of up to 20 pounds while remaining in the fixed position. To stabilize the arm under these conditions, the arm preferably comprises multiple articulated elongate links and a joining piece that substantially increases the friction fit of the arm to the mounting base so as to withstand a counter-force of up to 150 pounds.

28 Claims, 6 Drawing Sheets

FLEXIBLE STABILIZER ARM FOR FORCIBLY HOLDING AN OBJECT AGAINST A SURFACE

RELATED APPLICATIONS

This application claims priority under 35 U.S.C. §119(e) to U.S. Provisional Application Serial No. 60/175,300, filed Jan. 10, 2000, the contents of which are incorporated hereby by reference.

FIELD OF THE INVENTION

The present invention generally relates to flexible holding members that lock into a desired shape. More particularly, the present invention relates to flexible articulated arms useful for forceably holding an object against a surface, particularly an undulating surface.

BACKGROUND OF THE INVENTION

Flexible arms that can be adjusted to a desired position or attitude and then "locked" into position serve a variety of uses in industry and in medicine. For example, such devices are useful for holding a light at a desirable angle or location, or for holding an object against a grinding wheel. However, in practice it is difficult to keep the flexible arm from moving after it has been "locked" into position if it is used to hold or support a heavy object or when used to forceably hold an object against a surface, particularly against an undulating surface.

When adapted for attachment to a stationary object, such as a chest retractor, a flexible arm can be used during surgery for holding a medical device in a desired location. It has proven particularly difficult to obtain a flexible arm that can be used in this fashion to position and hold a device, such as a suction body, against the undulating surface of a beating heart while applying sufficient pressure to the surface of the heart to stabilize an area on the surface of the heart for surgery. The constant movement of the undulating surface tends to break down the "set" of the arm, leading to eventual loss of rigidity and even collapse.

If the surgical site is on the anterior side of the heart (when the patient is lying on his back), it would be desirable to have a stabilizer arm long enough to attach and stabilize the suction device against the anterior side of the heart. However, in an articulated flexible arm of multiple links, the longer the arm, the harder it is to keep the arm rigid once it is in place and locked into position. Each jointure between two links in the articulated arm is a potential site of movement, and the greatest moment of movement is at the jointure of the flexible arm to the base used to mount the arm upon a stationary object. This difficulty is compounded when the surface against which the arm is to be placed is in constant movement, such as the surface of a beating heart.

Accordingly, there is still a need in the art for flexible holding members that lock into a desired shape. More particularly, there is still a need in the art for flexible articulated arms useful for forceably holding an object against a surface, particularly an undulating surface.

BRIEF DESCRIPTION OF THE INVENTION

The present invention overcomes many of the problems in the art by providing stabilizer arm assemblies for forceably holding an object against a surface. The invention stabilizer arm assembly comprises a mounting assembly comprising a mounting base and moveable mounting clamp for removeably clamping the stabilizer arm assembly to a stationary fixture; a flexible arm attached to the mounting base, said flexible arm comprising multiple articulated elongate links with each link being rotatably joined to adjacent links; a turret joint comprising a freely rotatable socket attached to the distal-most link of the arm; a holding appendage fixedly joined to the turret joint; and a tightening mechanism loosely attaching together the mounting base, the multiple links of the arm, and the freely rotatable socket of the turret joint. Upon actuation of the tightening mechanism, the turret joint, the links of the arm and the mounting base are rigidly compressed together so as to hold the assembly in a fixed attitude while from about one to about twenty pounds of counter-force is applied against the appendage.

In another embodiment, the invention provides a stabilizer arm assembly comprising a mounting base; a flexible arm attached at the proximal end thereof to the mounting base, said flexible arm comprising a plurality of articulated links of graduated diminishing length from the proximal to the distal end thereof; a joining piece that enhances the friction in the jointure between the mounting base and the proximal-most link of the flexible arm; a turret joint comprising a freely rotatable socket, being attached to the distal-most link of the arm via the freely rotatable socket; an appendage fixedly attached to the turret joint; and a tightening mechanism loosely attaching together the mounting base, the joining piece, the plurality of links of the flexible arm, and the freely rotatable socket of the turret joint. Acutation of the tightening mechanism rigidly compresses together the turret joint, the links of the arm, the joining piece, and the mounting base so as to hold the assembly in a fixed attitude while from about one to about twenty pounds of counter-force is applied against the appendage and wherein the joining piece resists a greater force than the force at jointures between adjacent links of the arm.

DETAILED DESCRIPTION OF THE INVENTION

In accordance with the present invention, there are provided stabilizer arm assemblies for forceably holding an object against an undulating surface. In one embodiment, the invention stabilizer arm assembly comprises a mounting assembly comprising a mounting base and moveable mounting clamp for removeably clamping the stabilizer arm assembly to a stationary fixture; a flexible arm attached to the mounting base; a turret joint comprising a freely rotatable socket attached to the distal-most link of the arm; a holding appendage fixedly joined to the turret joint; and a tightening mechanism loosely attaching together the mounting base, the multiple links of the arm, and the freely rotatable socket of the turret joint. The flexible arm comprises multiple articulated elongate links with each link being rotatably joined to adjacent links. Upon actuation of the tightening mechanism, the turret joint, the links of the arm and the mounting base are rigidly compresses together so as to hold the assembly in a fixed attitude while from about one to about twenty pounds of counter-force is applied against the holding appendage.

In another embodiment, the invention provides a stabilizer arm assembly comprising a mounting base; a flexible arm attached at the proximal end thereof to the mounting base, said flexible arm comprising a plurality of articulated links of uniform or graduated diminishing length from the proximal to the distal end thereof; a joining piece that enhances the friction in the jointure between the mounting base and the proximal-most link of the flexible arm; a turret joint comprising a freely rotatable socket, being attached to the distal-most link of the arm via the freely rotatable socket; an appendage fixedly attached to the turret joint; and a tightening mechanism loosely attaching together the mounting base, the joining piece, the plurality of links of the flexible arm, and the freely rotatable socket of the turret joint. The flexible arm comprises multiple articulated elongate links with each link being rotatably joined to adjacent links. Acutation of the tightening mechanism rigidly compresses together the turret joint, the links of the arm, the joining piece, and the mounting base so as to hold the assembly in a fixed attitude while from about one to about twenty pounds of counter-force is applied against the appendage and wherein the joining piece resists a greater force than the force at jointures between adjacent links of the arm. For example, the force at the joining piece can be from about one pound to about 150 pounds.

In one embodiment, the tightening mechanism is actuated by advancing a tightening screw attached to the cable to increase tension in the cable, thereby forcing the links of the arm together, restricting motion of the links relative to one another. Thus, tightening of the tightening mechanism locks the multiple links into the desired position. To exert sufficient tension on the links to provide rigidity to the arm without breaking, the cable preferably has a breaking strength (to withstand high tensile force) in the range from about 500 to 1000 pounds force, such as 300 series corrosion resistant stainless steel.

Figure 1:
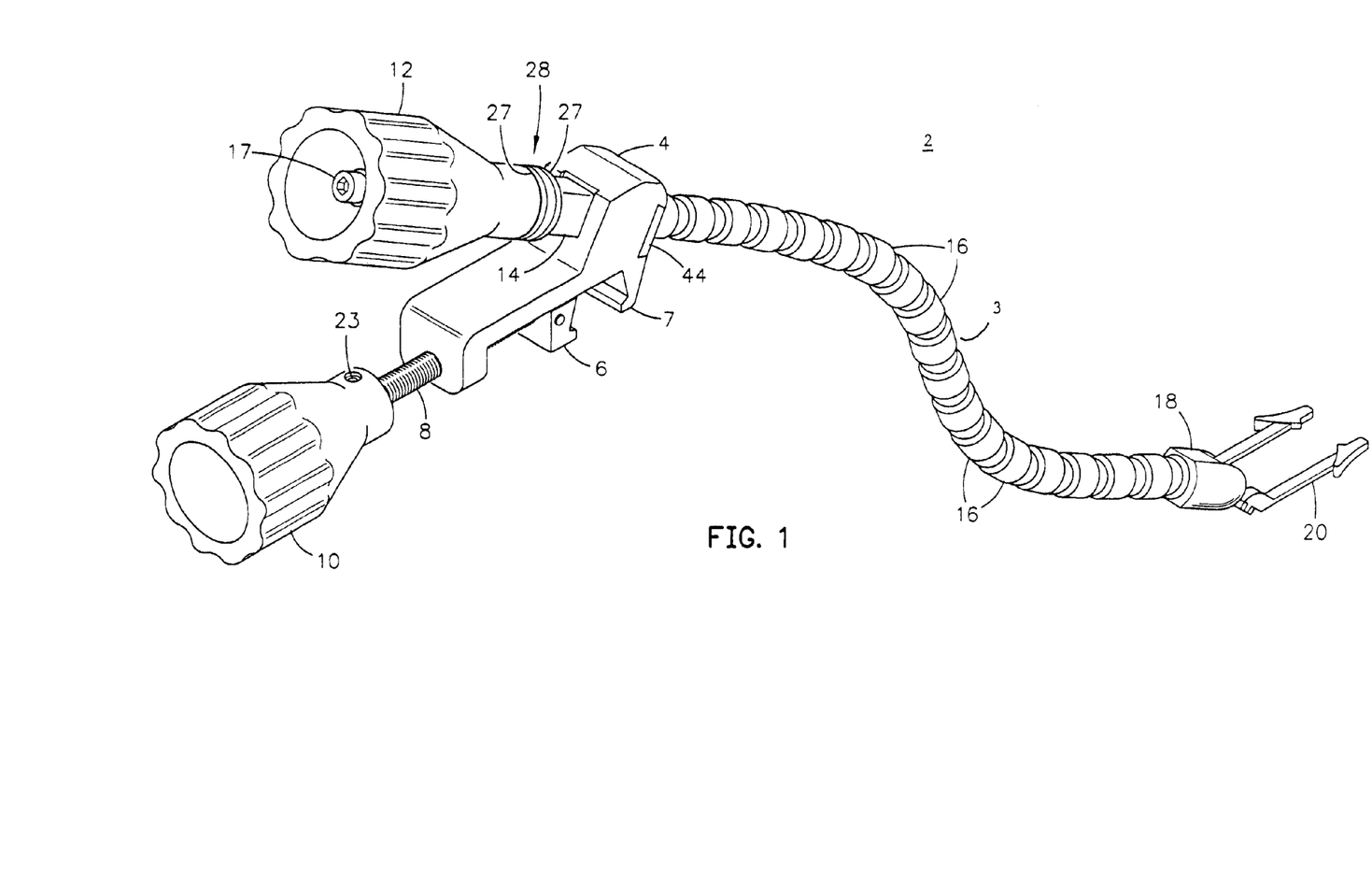
FIG. 1 is a perspective drawing showing the invention stabilizer arm assembly locked into a fixed attitude.
Figure 6:
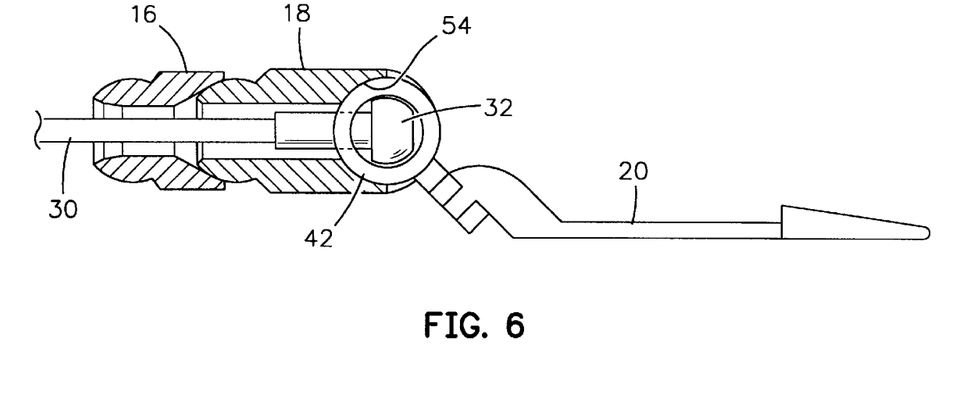
FIG. 6 is a cut-away drawing down the median of the distal end of the invention flexible arm assembly showing the cable ball riding within the turret joint and the appendage attached to the exterior of the turret joint.

The preferred embodiments of the invention flexible arm assembly are described with reference to FIGS. 1–5. As shown in FIG. 1, flexible arm assembly 2 comprises a flexible arm 3 having a plurality of links 16, ending at the distal tip in turret joint 50, which is comprised of spherical coupling 18 and appendage connector 42 (shown in detail in FIGS. 5 and 6), to which is attached appendage 20. The combination of spherical coupling 18 and appendage connector 42 forms turret joint 50. The flexible arm 3 is attached at the proximal end to mounting base 4. Tightening handle 12 is also attached to mounting base 4 via control screw 17, thrust bearing 22, and slideable connector 14, which is received into an internal bore within mounting base 4.

Mounting base 4 further comprises a mounting mechanism comprising fixed clamp foot 7, moveable clamp foot 6, and actuating clamp screw 8. Rotatable clamp screw handle 10 is rotated to advance moveable clamp foot 6 towards fixed clamp foot 7 to clamp the mounting assembly to a stationary fixture.

The flexibility of the flexible arm in the invention flexible arm assembly is increased by having segments of shorter length, but the shorter the segments, the less strength (e.g., the arm is more difficult to lock into a rigid position or will become unstable when a force is applied to the distal tip). The relative length and other dimensions of the links can be determined by the materials used to fabricate the arm (e.g., the weight of the materials), and the intended purpose. For example, it has been determined that, for an arm in an invention device intended for use in beating heart surgery (which requires a high degree of flexibility to position the arm accurately) the optimum combination of flexibility and strength is achieved by having multiple links of uniform size, for example about 0.5 inch in length or less for a total arm length of about 2 inches to 12 inches when fabricated of 316 grade stainless steel. This configuration results in uniform distribution of stress along the flexible arm, thus preventing excessive wear on any particular link. However, in another embodiment the links in the arm can have diminishing graduated length from the proximal to the distal end thereof. For example, a flexible arm comprised of the following set of links of graduated diminishing length from the proximal to the distal end of the arm has also proven useful: two links of one inch (located most proximally), two links of ¾ inch, and four links of ½ inch (located most distally), for a total of 5½ inches. At a length greater than about 12 inches (30 cm), even if the arm if fabricated of stainless steel, it has been found impossible to maintain the arm in a fixed position when a force as great as 12 pounds is applied against the distal tip (i.e., the appendage).

Preferably, to enhance flexibility of the arm, each link is rotatably joined to adjacent links. For example, as shown in cut-away in FIG. 2, links 16 of the flexible arm comprise a substantially cylindrical segment 34, with knob 36 at one end of the cylindrical segment of the link and concave socket 38 recessed into the opposite end of the cylindrical segment of the link. The knob at one end of the cylindrical link is received into the socket recessed at the end of an adjacent link so as to rotatably join to the adjacent link when the flexible arm remains loosened. However, when it is desired to fix the attitude of the arm prior to use by tightening the tightening mechanism, each jointure of two adjacent links is a potential site of movement. To aid in stabilizing the arm upon actuation of the tightening mechanism, at least a portion of the surface of the knobs 36 can be treated to increase the friction fit of the knobs into the sockets. For example, the surfaces of the knobs at the end of the links can be coated with a friction-inducing substance. However, it is possible that a surface coating will erode during use, forming flakes of coating. If the stabilizer assembly is to be used at a surgical site, the flakes of coating may be undesirable. Consequently, in this situation, it is preferred to roughen at least part of the surface of the knobs in the flexible arm to increase the friction fit of the knob 36 into the socket of the adjoining link. For example, metal knobs can be scored with a fine pattern by turning the knobs at low speed to cut a groove pattern in the knobs.

Figure 2:
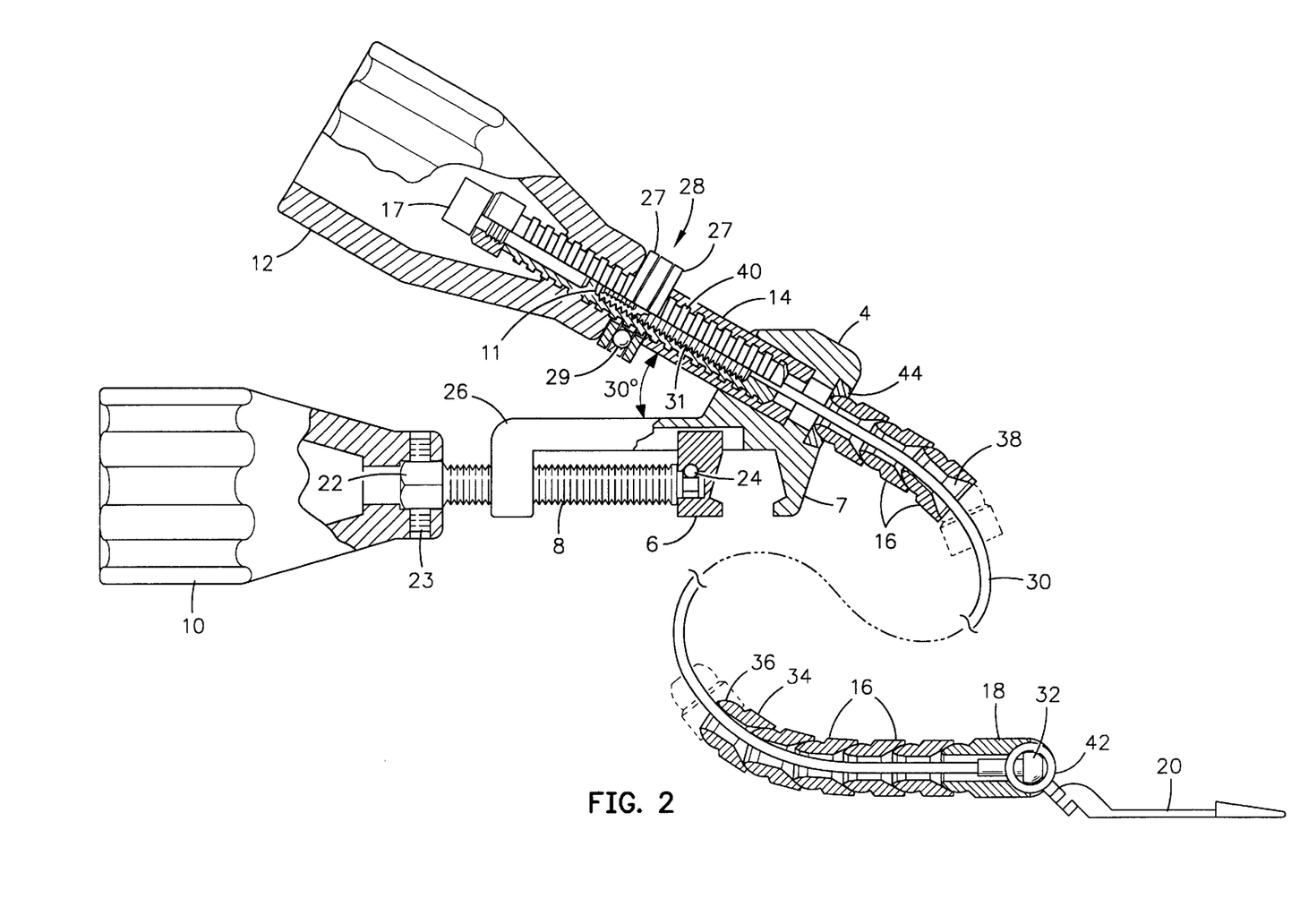
FIG. 2 is a cut-away drawing showing the tightening mechanism running down the central axis of the flexible arm. At the distal end of the cable assembly, a ball attached to the distal end of the cable is held within the turret joint, to which an appendage (foot) is fixedly attached. A cut-away of the clamping handle shows the mechanism of the clamping screw, which is used to removeably attach the flexible arm assembly to a stationary fixture.

Preferably, the knobs of the links of the flexible arm have a generally convex (e.g., substantially spherical) portion that attaches to the cylindrical portion of the link, but are more flattened at the head of the knob (the portion most distant from the cylindrical portion of the link). The sockets in the cylindrical portion of the links can have a corresponding concave shape (e.g., semi-spherical) to receive the convex knobs. Due to the knob and socket jointures between the links of the arm, the flexible arm is freely deformable in three dimensions and/or can assume an "O" or "S" shape, if desired, as shown in FIG. 2. In other words, the flexible arm can have up to 360° of curvature along its length and can flex in a sideways motion as well as in a vertical plane.

The segments (i.e., links 16) of the flexible arm can be manufactured of any substance having sufficient hardness and strength for the intended purpose. The jointure of the flexible arm to the rigid mounting base is the point that experiences the greatest force when the arm is locked into a fixed position and a counter-force is applied against the distal tip of the arm, e.g., via an appendage fixed at the distal tip. To further provide strength and rigidity when the arm is locked into position, the invention flexible arm assembly further comprises a joining piece 44 located at the jointure of the flexible arm 3 to the rigid mounting base 4. The joining piece 44 is designed to enhance friction in the jointure between the mounting base 4 and the proximal-most link 16. Preferably, the joining piece is made of hardened metal (i.e. a metal harder than that used to fabricate the proximal most link) and is positioned to be replaceable. For example, if the articulated arm is comprised of multiple links joined together in a knob and socket assembly, as described above, the joining piece 44 can consist of a plate or disc having a many-sided opening 45 into which the knob of the proximal-most link is forceably compressed upon actuation of the tightening mechanism. Preferably the opening 45 in the joining piece is a double hex arranged to provide points and valleys around the opening so that the points will dig into the proximal-most link of the flexible arm when tightened. In this embodiment, the jointure of the proximal-most link to the mounting base can withstand a force of from about one pound to about 150 pounds while the joining piece substantially eliminates movement of the arm with respect to the mounting base. In alternative embodiments the opening can have from about 6 to about 30 sides. The many-sided opening 45 provides a greater resistance to movement of the knob within the opening than would a smooth and curvilinear opening.

Figure 3:
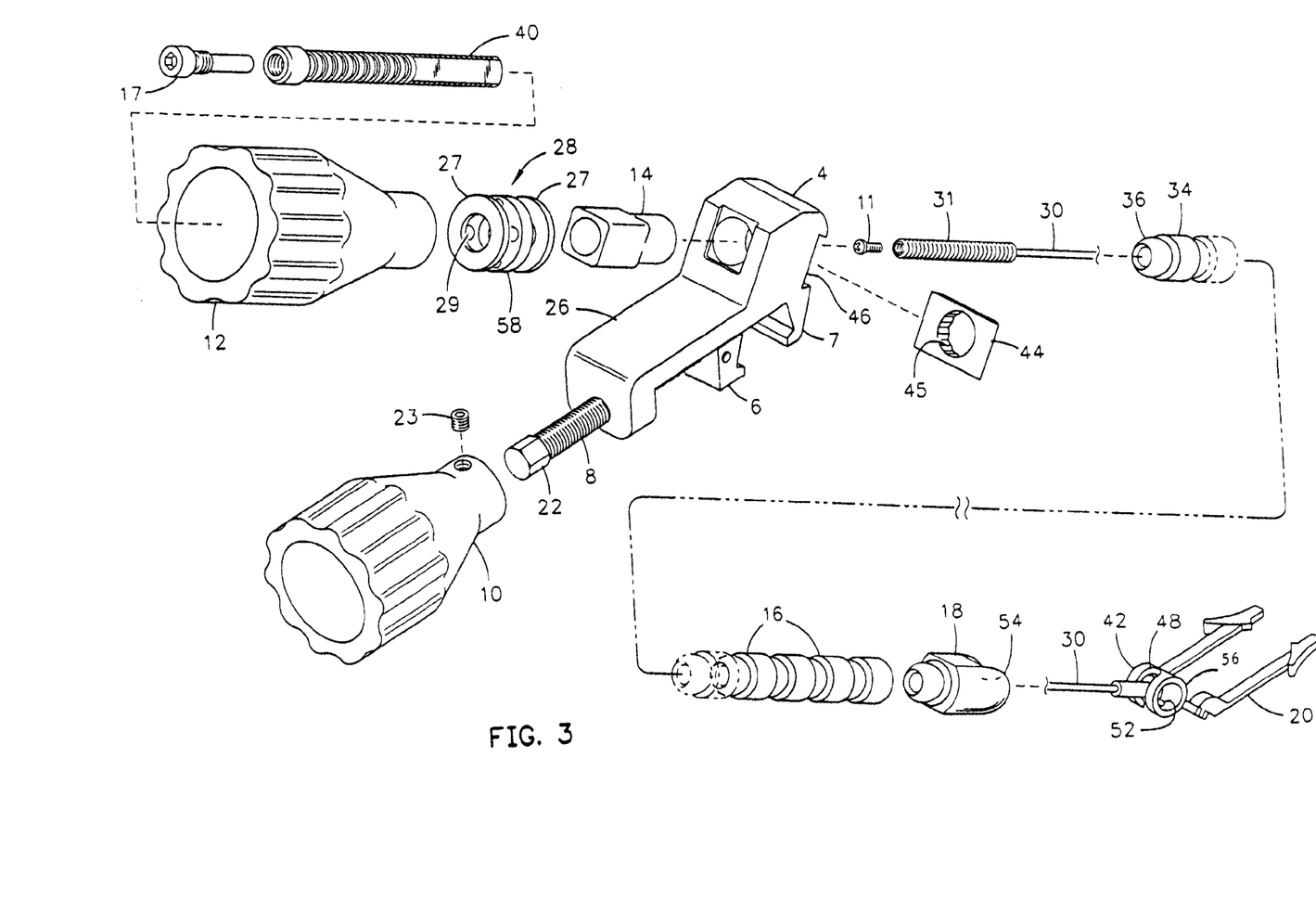
FIG. 3 is an exploded drawing showing a preferred embodiment of the invention flexible arm assembly.
Figure 4:
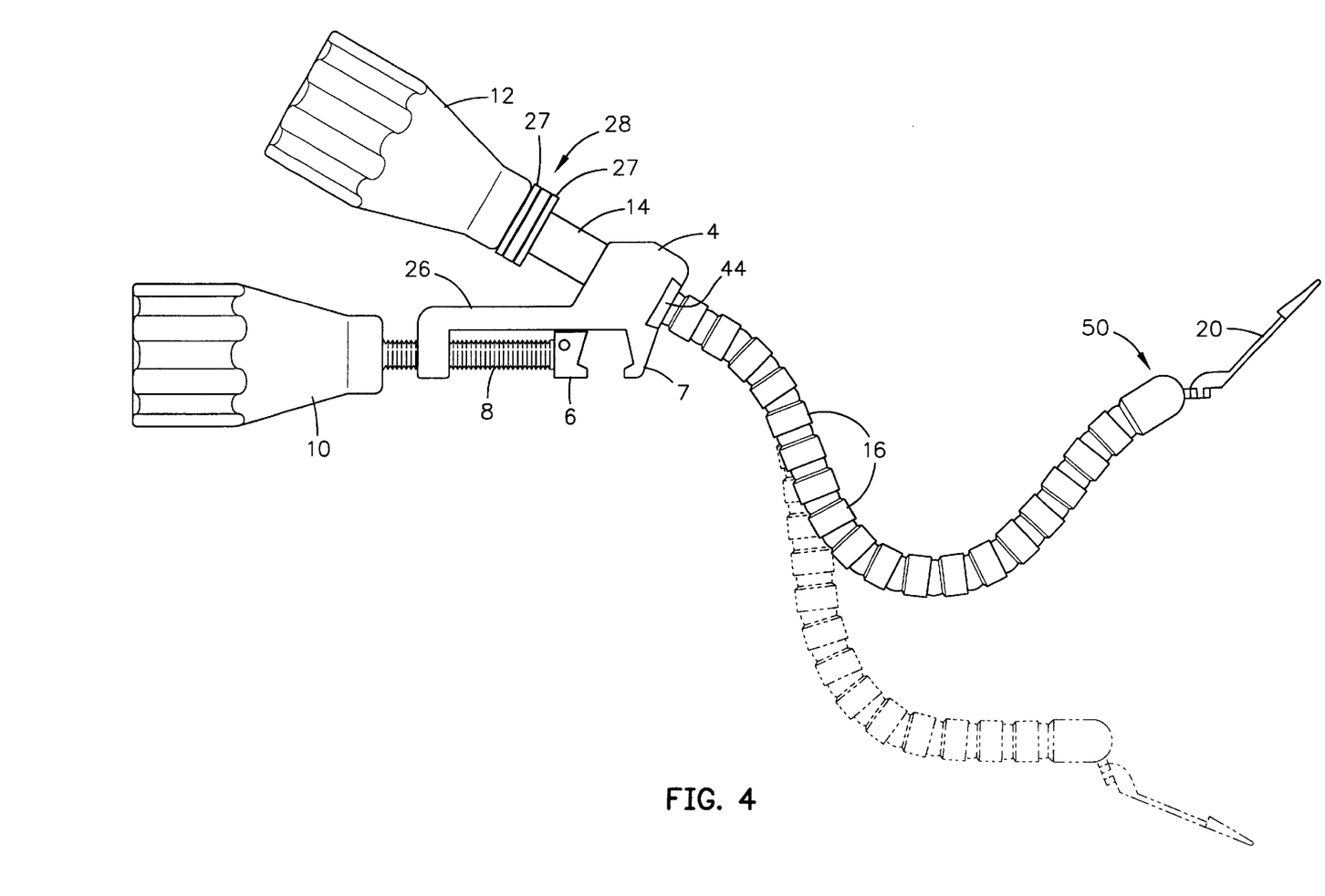
FIG. 4 is a schematic drawing showing the invention flexible arm locked into a fixed attitude by actuation of the tightening mechanism. The position of the flexible arm prior to positioning and actuation of the tightening mechanism is shown in phantom (dotted lines).
Figure 5:
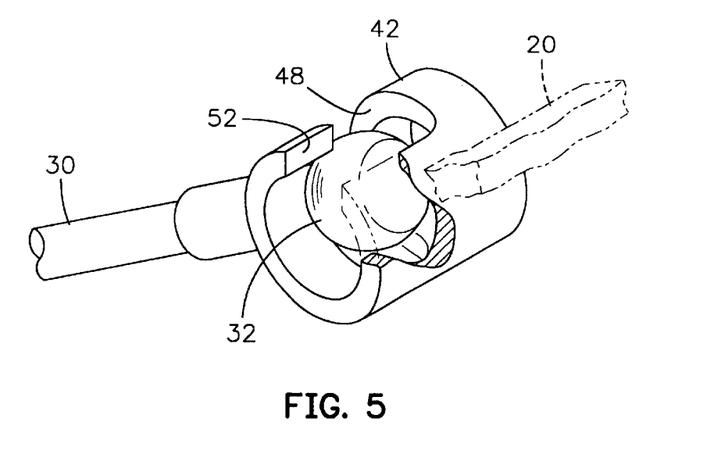
FIG. 5 is an isometric drawing showing in partial cutaway the cable ball captured within the cylindrical connector in the turret joint. The appendage, which is is attached to the exterior of the connector is shown in phantom.

As shown in FIG. 3, the joining piece 44 is a plate that slides into a slot 46, which as beveled edges to replaceably hold the joining piece into the slot cut in mounting base 4. Because the joining piece is many-sided rather than curvilinear, the knob in the socket within the mounting base will be more restricted in movement by the joining piece than are the knobs in the curvilinear sockets in the balance of the flexible arm, thus providing enhanced rigidity to the invention assembly at the point of greatest force during use of the assembly to hold an object against a surface, such as an undulating surface.

As also shown in FIG. 3, connector 42 is permanently attached to the proximal end of appendage 20 (shown here as a forked foot). For example, connector 42 can be welded to appendage 20. As further shown in detail in FIGS. 5 and 6, the turret joint 50 is formed by spherical coupling 18 at the distal tip of the flexible arm 3 and appendage connector 42 so as to attach appendage 20 to flexible arm 3 in a freely rotatable manner (i.e., to flex in a vertical plane as well as to freely rotate or spin at the end of the flexible arm) until the tightening mechanism is actuated. Spherical coupling 18 comprises a knob that fits into the concave recess of its adjoining link in the arm, a cylindrical middle portion, and a distal portion with semi-spherical socket 54 for receiving the cylindrical-shaped portion 56 of appendage connector 42. Connector 42 comprises a cylindrical-shaped portion with internal bore sized to receive the ball of the cable and which has a slot-like cut-out 48 running semi-circumferentially around the side of the cylinder, providing an opening that connects with the internal bore. An additional cut out 52 is at right angles to the slot-like cut-out 48 and is sized to allow the cable to slide through cut out 52 while ball 32 is received into the bore of cylindrical connector 42.

Ball 32 at the distal end of cable 30 (shown in FIG. 2) is preferably a ball and shank fitting which is swaged onto the end of cable 30. Ball 32 is held within pivot joint 50 by the sides of the semi-spherical socket 54 in spherical coupling 18 and pivots or rotates 360° within the bore of the cylindrical connector 42 while the cable translates along slot-like cut-out 48, giving a deflection of the appendage (like a foot at an ankle joint), for example a deflection of up to about 120° as shown here. Thus the appendage is freely rotatable within the pivot joint and has a large range of flexure to facilitate accurate positioning of the appendage against any contour of a surface until the arm and turret joint is locked into a fixed attitude by actuation of the tightening mechanism. Ball 32 can be modified by placing a flat on the surface closes to the shank to move and spread the force away from the slot in connector 42.

The tightening mechanism connects together the distal portion of the arm and the proximal end of the stabilizer assembly (e.g., the mounting base) and locks the links of the flexible arm into a fixed attitude. Before tightening, the connection between the various parts of the assembly are loosely joined by the cable, which connects together mounting base 4, the plurality of links 16 of the flexible arm, and the freely rotatable socket of the turret joint 50 via cable 30 and ball 32. Upon actuation of the tightening mechanism, the turret joint, the links of the arm and the mounting base are rigidly compressed together so as to hold the assembly in a fixed attitude while from about one to about twenty pounds, for example from about five to about twelve pounds, of counter-force is applied against the holding appendage.

More particularly, as shown in exploded view in FIG. 3, the tightening mechanism comprises (from proximal to distal end) control screw 17, draw bar 40, cable 30 with internal, security screw 11 (that screws into internal threads along the proximal-most end of exteriorly threaded and swaged portion 31 of cable 30) and cable ball 32, which is fixedly attached at the distal end of cable 30. The proximal portion of draw bar 40 is generally cylindrical with an interior bore and external threads that mate with internal threads along an internal bore within handle 12. However, the distal portion of draw bar 40 has flatted sides and the interior bore is lined with internal threads that mate with the external threads on the threaded and swaged portion 31 of cable 30. Preferably, the external threads on the draw bar and the mating internal threads on handle 12 are acme threads for added strength while the internal threads along the bore of draw bar 40 and the mating external, swaged threads along the threaded portion 31 of cable 30 are pointed.

When the assembly is assembled as shown in FIG. 1, slideable connector 14 is used to join together draw bar 40, handle 12 and the flexible arm threaded through with the cable assembly and attached appendage. Slideable connector 14 has a distal end with a cylindrical exterior portion and an interior bore with flatted sides designed to receive the distal end (with mating flatted sides) of draw bar 40. The cylindrical exterior portion of connector 14 is sized to slide into a bore hole through mounting base 4. Slideable connector 14 also comprises a proximal portion with a smooth interior bore and squared exterior sized to sit flush against the exterior of distal washer 27. The proximal, threaded portion of cable 30 is passed through an interior smooth bore in connector 14 through washers 27 and thrust bearing 28 and the bore of handle 12. Draw bar 40 passes through the large opening the in proximal end of handle 12 and is threaded via the exterior threads thereon into the mating interior threads in the bore of handle 12. The thrust bearing 28 is a three piece assembly of two washers 27 and a set of steel bearings 29, which are encased in a slightly compressible material, such as nylon. Thrust bearing 28 facilitates rotation of the tightening handle 12 as the various parts of the assembly are compressed together by effective shortening of the cable (i.e., by advancement of the threaded portion 31 of cable 30 proximally within the draw bar). Thrust bearing 28 compresses somewhat as the tightening mechanism is tightened to prevent sudden application of greater tensile force than can be tolerated by the assembly.

When handle 12 is rotated, the threaded portion of the cable advances proximally up the handle, while the handle advances distally along the draw bar. Security screw 11, which screws into the interior threads at the proximal end of the threaded portion of the cable, also fits into a recess in the proximal end of draw bar 40 and is sized with respect to the interior bore of the draw bar to lodge against shoulders therein created by a small decrease in the internal diameter of the interior bore in the draw bar. Thus, security screw 11, which is inserted into the end of the cable assembly using a long handled Allen wrench applied through the proximal opening of handle 12, functions to prevent backthreading of the cable completely out of the draw bar. Control screw 17, which is inserted last, has a hex head for receiving an Allen wrench and screws into the interior threads at the proximal end of the draw bar. Control screw 17 functions to keep alignment of the assembly and to prevent threading of the cable too far into the draw bar.

Cable 30 can be manufactured of any substance having sufficient tensile strength to provide the invention flexible arm assembly with the capability to remain rigid when up to about twenty pounds of counter-force is applied against its tip (e.g. against an appendage attached at its tip or against an instrument held by the appendage against an undulating surface). For example, a 300 Series corrosion resistant stainless steel wire rope cable having a breaking strength rating of 920 pounds has been found to provide the strength needed for a flexible arm of about 9 inches in length.

The appendage can be in any shape adapted to the particular use to which the stabilizer arm assembly is to be put, such as a grabber, clipper, scissors, flat blade, and the like. In a preferred embodiment, as illustrated herein, the appendage 20 is a forked foot with two tines. In this embodiment, the two-tined stabilizer foot is shaped to be threaded through attachment sites located in a flexible suction body such as is described in copending U.S. patent application Ser. No. 09/293,334, filed Apr. 16, 1999, which is incorporated herein by reference in its entirety. In this embodiment, the stabilizer arm assembly is adapted to hold a suction body against the undulating surface of a beating heart during an "off pump coronary artery bypass" (OPCAB) procedure to perform an anastomosis. Preferably, the invention stabilizer arm assembly is sized and adapted for use wherein the undulating surface is on the anterior side of the beating heart.

As shown in FIGS. 1–3, the mounting base 4 of the stabilizer arm assembly includes a clamp actuated by a rotatable clamp screw for removeably attaching the stabilizer arm assembly to a stationary fixture. As seen in cut-away in FIG. 2, the clamping mechanism is actuated by turning rotatable clamping handle 10, which mates with the many-sided head 22 of the clamp screw 8 to advance moveable clamp foot 6 towards fixed clamp foot 7. Set screws 23 abut against opposite sides of head 22 and can be removed to remove clamping handle 10 for sterilization of the assembly, if desired. Set pin 24 is recessed within moveable clamp foot 6 and rides within a groove encircling the distal end of clamp screw 8 to force moveable foot 6 to advance towards fixed foot 7 as clamp screw 8 is rotated. In an alternative embodiment, the handles or interchangeable or a single handle can be used as the clamp tightening handle and the tightening handle. In this embodiment a nut used to attach the handle to the draw bar such that the nut move downs the draw bar as the tightening handle is rotated while the draw bar does not rotate. The bore in the handle is also dimensioned to attach to the head of the clamp screw. In this embodiment, the handle can readily be used to perform either function and then can be removed from the assembly for convenience during use.

The handles can be of any convenient size that does not interfere with use of the assembly. For example, if the invention assembly is to be used in surgery, it is convenient for the surgeon if the handles are about 3 inches in length and has a cross-sectional diameter at its largest dimension of about 2 inches to about 3 inches for ease in placing the flexible arm into a desired position at a treatment site, for example, for forceably holding a suction body in place on the surface of a beating heart. To avoid excessive weight, the handle can be partially hollow and can be fabricated of such materials as plastic or bakelite, and the like, by injection molding. Alternatively, the handle can be machined from metal or plastic, and the like, using techniques known in the art. In a preferred embodiment, tightening handle 12 is injection molded from Delrin 500 plastic and, for convenience during use is positioned at an angle of from about 0° to about 90° with respect to the face of the mounting base 4 at the point of attachment, for example at an angle of about 30° to about 45°. In this embodiment, the mounting clamp is preferably designed with dimensions compatible with most adult cardiac retractors. For example, the clamp is about 0.8 inch (2 cm) wide and accommodates rectangular sections ranging in thickness of 0.125 inch (0.32 cm) to 0.4 inch (1/02 cm) and widths of 0.25 inch to 1.5 inch (3.81 cm).

Figure 7:
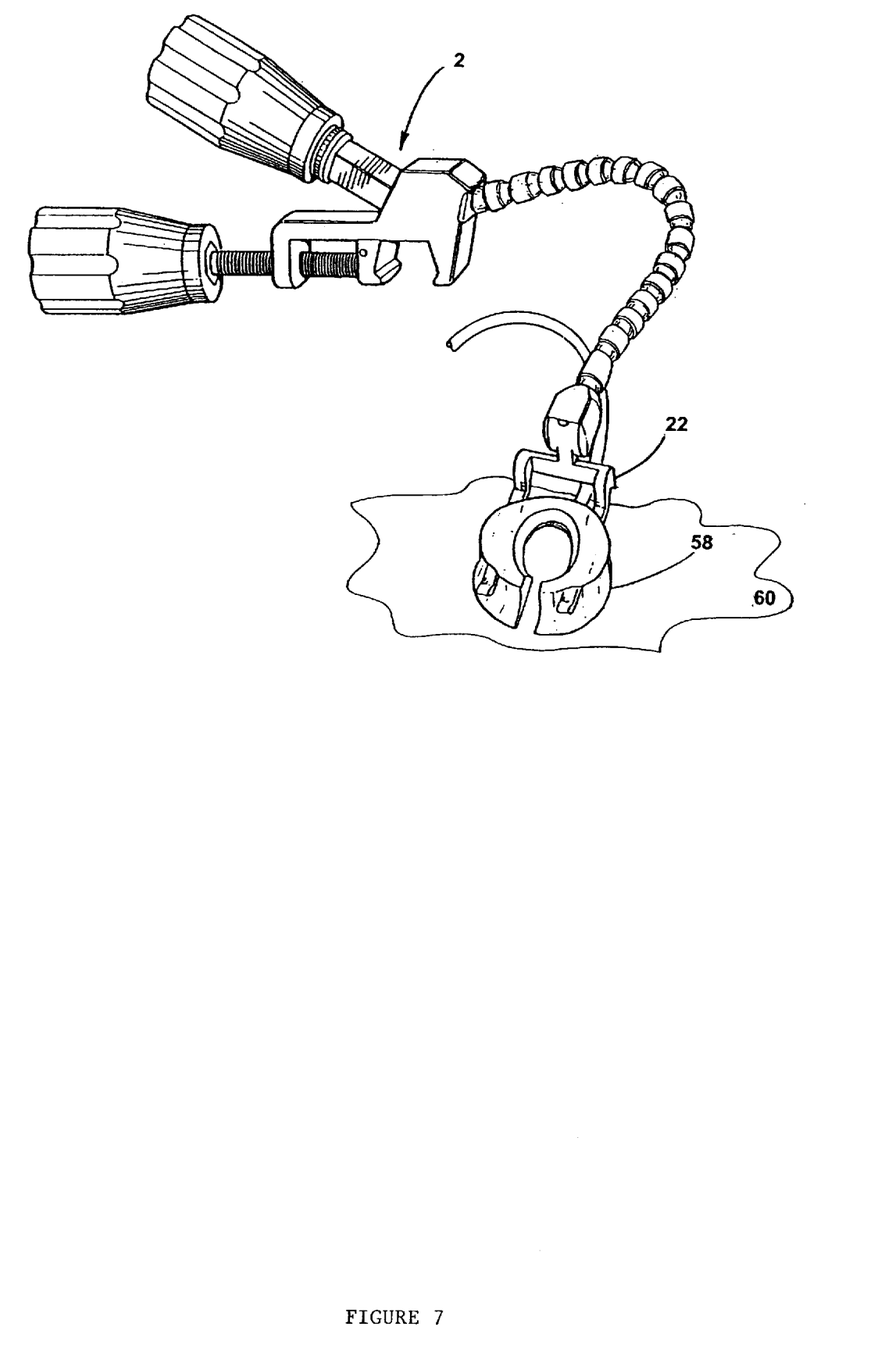
FIG. 7 is a drawing showing the invention stabilizer arm assembly with the appendage holding a cardiac suction body against the surface of a beating heart.

The flexible arm of invention stabilizer assemblies can be manipulated three-dimensionally, e.g., manually, to assume a desired shape and then are locked into whatever attitude is present when the tightening mechanism is actuated. However, once locked into a desired position, the arm becomes substantially rigid both along its length and at the point of greatest stress, i.e., the jointure of the arm to the mounting base. These attributes particularly suit the invention devices for holding an appendage attached to the turret joint (or an object 58 attached to or held by the appendage 20) against any type of undulating surface 60. For example, as shown in FIG. 7, a preferred use of the invention stabilizer assembly is for forcibly holding a cardiac suction device 58 motionless against surface 60 of a beating heart to stabilize the site for surgery. In other embodiments, the invention device can be used to hold an object against a grinding wheel during a grinding procedure, and the like.

For illustrative purposes the various parts of the flexible arm assembly have been fabricated from the following materials: Links 16 of the flexible arm are fabricated from 316 stainless steel, as are the appendage 20 and draw bar 40; joining piece 44 is fabricated from 17-4 stainless steel hardened; cable 30 is 300 series corrosion resistant stainless steel; set screws set pins and security screw are fabricated from 18-8 stainless steel and all other parts (except for the handles and the bearing housing in the thrust bearing) are fabricated from 18-8 stainless steel. However, various corrosion-resistant, hardened metallic materials, such as stainless steel, titanium, and the like, can be used when it is desired to machine the various parts of the invention flexible arm assembly. Alternatively, plastics or composites having comparable properties of strength and hardness can also be used to fabricate various parts of the assembly by methods known in the art, such as injection molding.

In the preferred embodiment, the flexible arm assembly is designed for repeated use (e.g., in medical applications) and hence is readily adapted to be sterilized for reuse. To facilitate sterilization, the tightening assembly can be loosened by rotating the tightening handle so as to partially backthread the cable out of the draw bar until the cable is visible between the links and connector 14 slides out of the mounting base. The security screw will prevent backthreading of the cable to the point that the apparatus comes apart. In this loosened state the assembly can readily be scrubbed to remove debris that may have lodged in the links. In addition, in embodiments wherein the assembly is manufactured of hardened metals, the complete assembly can be steam sterilizable. For example, in the preferred embodiment described herein, the assembly can be steam sterilized unwrapped at a temperature of about 132° C., for 10 minutes in a gravity air displacement instrument. For a double wrapped instrument (double wrapped using a single use, non-woven, lint free fabric for sterile good wrapping), a suitable steam-cleaning temperature is 121° C. for 30 minutes. When properly cared for as described herein, the invention flexible arm assembly can be reused (e.g., tightened, loosened and sterilized) a multitude of times, for example about 500 to 1000 times.

The invention flexible arm assembly can be lubricated to facilitate use, for example by complete immersion in a water-soluble lubricant for 30 seconds. Suitable lubrication agents are high viscosity lubricants that cling to the surface of metal when steam autoclaved, e.g. PRESERVE™ Instrument Mild (Johnson & Johnson-Codman, Catalog No. 43-1033).

While the invention has been described in detail with reference to certain preferred embodiments thereof, it will be understood that modifications and variations are within the spirit and scope of that which is described and claimed.

What is claimed is:

1. A stabilizer arm assembly for forcibly holding an object against a surface, said assembly comprising:
    a mounting assembly comprising a mounting base and moveable mounting clamp for removably clamping the stabilizer arm assembly to a stationary fixture;
    a flexible arm attached to the mounting base, said flexible arm comprising multiple articulated elongate links with each link being rotatably joined to adjacent links, where said and link has a substantially cylindrical segment with a knob attached at one end of the cylindrical segment and a socket at the other end of the cylindrical segment for receiving the knob of an adjacent link in the arm so as to rotatably join to the adjacent link;
    a joining piece comprising a plate with a many-sided, centrally located opening therein for forcibly receiving the knob of the proximal link;
    a turret joint comprising a freely rotatable socket attached to the distal link of the arm;
    a holding appendage fixedly joined to the turret joint for holding the object; and
    a tightening mechanism loosely attaching together the mounting base, the multiple links of the arm, and the freely rotatable socket of the turret joint;
    wherein the appendage flexes in a vertical plane as well as freely spins through 360° within the turret joint prior to actuation of the tightening mechanism, and wherein actuation of the tightening mechanism rigidly compresses together the turret joint, the links of the arm and the joining piece so as to hold the assembly in a fixed attitude while from about one to about twenty pounds of counter-pressure is applied against the holding appendage.

2. The stabilizer arm according to claim 1 wherein the object is a surgical instrument and the surface is a beating heart.

3. The stabilizer arm assembly according to claim 2 wherein the tightening mechanism further comprises a tightening screw assembly attached at the distal end to the cable and at the proximal end to a rotatable, replaceable handle for advancing the screw so as to shorten effective length of the cable, thereby compressing together the links of the flexible arm.

4. The stabilizer arm assembly according to claim 3 wherein the tightening screw assembly can be sufficiently loosened for cleaning to completely expose each link in the flexible arm without allowing the flexible arm assembly to fall apart.

5. A stabilizer arm assembly comprising:
    a mounting base;
    a flexible arm attached at the proximal end thereof to the mounting base, said flexible arm comprising a plurality of articulated links of uniform or graduated diminishing length from the proximal to the distal end thereof;
    a joining piece joining the mounting base to the flexible arm, wherein the joining piece has a many-sided opening that forcibly receives the proximal link of the flexible arm;
    a turret joint comprising a freely rotatable socket, being attached to the distal link of the arm via the freely rotatable socket;
    an appendage attached to the turret joint; and
    a tightening mechanism loosely attaching together the mounting base, the joining piece, the plurality of links of the flexible arm, and the freely rotatable socket of the turret joint;
    wherein the appendage flexes in a vertical plane as well as freely spins through 360° within the turret joint prior to actuation of the tightening mechanism, and wherein actuation of the tightening mechanism rigidly compresses together the turret joint, the links of the arm, the joining piece, and the mounting base so as to hold the assembly in a fixed attitude while from about one to about twenty pounds of counter-force is applied against the appendage and wherein the joining piece resists a greater force than the force at jointures between adjacent links of the arm.

6. The stabilizer arm assembly according to claim 5 wherein the counter-force is an undulating force.

7. The stabilizer arm assembly according to claim 5 wherein the force at the joining piece is from about one pound to about 150 pounds.

8. The stabilizer arm assembly according to claim 5 wherein the articulated links have a graduated diminishing length from the proximal to the distal end of the flexible arm and the flexible arm is from about 2 inches to about 12 inches in length.

9. The stabilizer arm assembly according to claim 5 wherein each link is rotatably joined to adjacent links.

10. The stabilizer arm assembly according to claim 5 wherein at least part of the surface of the knob is treated to increase the friction fit of the knob into the socket.

11. The stabilizer arm assembly according to claim 5 wherein the joining piece is a plate with a many-sided, centrally located opening therein for forcibly receiving the knob of the proximal link.

12. The stabilizer arm assembly according to claim 11 wherein the joining piece is recessed into a slot in the mounting base to restrict movement of the knob of the proximal link within the socket in the mounting base upon actuation of the tightening mechanism.

13. The stabilizer arm assembly according to claim 12 wherein the joining piece is fabricated of harder metal than the knob of the proximal link.

14. The stabilizer arm assembly according to claim 13 wherein the joining piece replaceably slides into the slot in the mounting base.

15. The stabilizer arm assembly according to claim 14 wherein the tightening mechanism comprises a rotatable tightening screw attached to a tightening cable, whereby rotation of the screw actuates the tightening mechanism to fix the attitude of the arm and turret joint.

16. The stabilizer arm assembly according to claim 15 wherein said each of the plurality of links contains a hollow opening and the cable is threaded through the hollow openings to connect between the mounting base and the turret joint.

17. The stabilizer arm assembly according to claim 16 wherein the turret joint comprises a cylindrical segment with a semi-circular slot in the side of the cylindrical segment and the cable of the tightening mechanism has a ball at the distal end thereof that pivots or rotates within the cylindrical segment and the cable translates along the slot prior to actuation of the tightening mechanism.

18. The stabilizer arm assembly according to claim 5 wherein the tightening mechanism is connected between the distal end of the arm and the mounting base.

19. The stabilizer arm assembly according to claim 5 wherein deflection of the arm is curvilinear along the arm through an arc up to 360° and actuation of the tightening mechanism fixes the arm in such curvilinear attitude.

20. The stabilizer arm assembly according to claim 19 wherein deflection of the arm at the joining piece is from about 20° to 90° with respect to the face of the mounting base.

21. The stabilizer arm assembly according to claim 5 wherein deflection of the arm is three dimensional.

22. The stabilizer arm assembly according to claim 5 wherein the mounting base comprises a moveable clamp for removeably attaching the assembly to a stationary fixture.

23. The stabilizer arm assembly according to claim 5 wherein the appendage is a forked foot with tines for holding an object against a surface.

24. The stabilizer arm assembly according to claim 23 wherein the object is a cardiac suction body.

25. The stabilizer arm assembly according to claim 5 wherein deflection of the appendage at jointure with the turret joint is through a vertical angle of up to 120° prior to actuation of the tightening mechanism.

26. The stabilizer arm assembly according to claim 5 wherein the stabilizer arm assembly is constructed of stainless steel.

27. The stabilizer arm assembly according to claim 5 wherein the stabilizer arm assembly is steam sterilizable for reuse.

28. The stabilizer arm assembly according to claim 27 wherein the stabilizer arm assembly is steam sterilizable unwrapped at a temperature of about 132° C., for 10 minutes.

* * * * *